United States Patent
Augeri et al.

(10) Patent No.: US 8,153,804 B2
(45) Date of Patent: Apr. 10, 2012

(54) ARYL PYRIDINES AND METHODS OF THEIR USE

(75) Inventors: David J. Augeri, Princeton, NJ (US); James E. Tarver, Jr., Morrisville, PA (US); Qinghong Fu, Plainsboro, NJ (US); Michael Victor Voronkov, Pennington, NJ (US); Doan Hackley, San Diego, CA (US); Michael E. Mertzman, Belmont, CA (US); Marianne Carlsen, Yardley, PA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 1012 days.

(21) Appl. No.: 11/497,539

(22) Filed: Jul. 31, 2006

(65) Prior Publication Data

US 2007/0032501 A1   Feb. 8, 2007

Related U.S. Application Data

(60) Provisional application No. 60/704,742, filed on Aug. 2, 2005.

(51) Int. Cl.
| | |
|---|---|
| C07D 213/38 | (2006.01) |
| C07D 417/10 | (2006.01) |
| C07D 401/04 | (2006.01) |
| C07D 401/10 | (2006.01) |
| C07D 213/73 | (2006.01) |
| A61P 35/00 | (2006.01) |

(52) U.S. Cl. ............. 546/194; 544/238; 546/270.7; 546/277.7; 546/268.4; 546/311

(58) Field of Classification Search ............. 546/194, 546/268.4, 269.7, 277.1, 311, 270.7, 277.7
See application file for complete search history.

(56) References Cited

U.S. PATENT DOCUMENTS

| | | | |
|---|---|---|---|
| 5,346,906 | A | 9/1994 | Baker et al. |
| 5,952,349 | A | 9/1999 | Asberom et al. |
| 6,096,766 | A | 8/2000 | Baker et al. |
| 6,294,504 | B1 | 9/2001 | Tobler et al. |
| 6,458,789 | B1 | 10/2002 | Forood et al. |
| 6,500,956 | B1 | 12/2002 | Geissler et al. |
| 6,521,606 | B2 | 2/2003 | Sorensen et al. |
| 6,887,875 | B2 | 5/2005 | Huang et al. |
| 2003/0082191 | A1 | 5/2003 | Poduslo et al. |
| 2004/0023973 | A1 | 2/2004 | Nagato et al. |
| 2004/0029857 | A1 | 2/2004 | Hale et al. |
| 2004/0053927 | A1 | 3/2004 | Darrow et al. |
| 2004/0082627 | A1 | 4/2004 | Darrow et al. |
| 2004/0097531 | A1 | 5/2004 | Ledeboer et al. |
| 2004/0097563 | A1 | 5/2004 | Murata et al. |
| 2004/0186115 | A1 | 9/2004 | Ledeboer et al. |

FOREIGN PATENT DOCUMENTS

| | | |
|---|---|---|
| EP | 0943032 | 9/2000 |
| JP | 05058997 | 3/1993 |
| JP | 2001081074 | 3/2001 |
| JP | 2004107271 | 4/2004 |
| JP | 2004182713 | 7/2004 |
| JP | 2004359642 | 12/2004 |
| WO | WO 95/29155 | 11/1995 |
| WO | WO 98/01425 | 1/1998 |
| WO | WO 98/06691 | 2/1998 |
| WO | WO 98/26127 | 6/1998 |
| WO | WO 02/100838 | 12/2002 |
| WO | WO 2004/043926 | 5/2004 |
| WO | WO 2004/055015 A1 | 7/2004 |
| WO | WO 2004/089910 | 10/2004 |
| WO | WO 2004/096131 | 11/2004 |
| WO | WO 2004/096135 | 11/2004 |

OTHER PUBLICATIONS

Griesser, Chapter 8, The Importance of Solvates (pp. 211-230), Polymorphism: In the Pharmaceutical Industry, R. Hilfiker, ed.; Wiley-VCH 2006.*
Smits, et al., 24th Euro. Crystalligraphic Meeting, ECM24, Marrakech, 2007, p. s208.*
Shaihla et al., Indian J. Pharma. Sci., 1990, 52(1), 13-15.
Murata, T. et al., Discovery of Novel and Selective IKK-B Serine-Threonine Protein Kinase Inhibitors, Part 1, Bioorg. & Med. Chem. Letters 13 (2003) 913-919.
Murata, T. et al., Synthesis and Structure-activity Relationships of Novel IKK-B Inhibitors, Part 2, Bioorg. & Med. Chem. Letters 14 (2004) 4013-4017.
PCT Search Report and Written Opinion, Jan. 22, 2007, Lexicon Genetics.

* cited by examiner

Primary Examiner — James O Wilson
Assistant Examiner — Cecilia M Jaisle
(74) Attorney, Agent, or Firm — Max Bachrach

(57) ABSTRACT

Aryl pyridines, compositions comprising them, and methods of their use for the treatment, prevention and management of a variety of diseases and disorders are disclosed.

15 Claims, No Drawings

ARYL PYRIDINES AND METHODS OF THEIR USE

This application claim priority to U.S. provisional application No. 60/704,742, filed Aug. 2, 2005, the entirety of which is incorporated herein by reference.

1. FIELD OF THE INVENTION

This invention relates to aryl pyridines and related compounds, and methods of their use for the treatment, prevention and/or management of various diseases and disorders.

2. BACKGROUND

Protein kinases (PKs) are enzymes that catalyze the phosphorylation of hydroxyl groups on tyrosine, serine and threonine residues of proteins. The phosphorylation of proteins modulates various cell activities such as cell growth, differentiation and proliferation. Abnormal PK activity has been related to a host of disorders, ranging from relatively non-life threatening diseases such as psoriasis to extremely virulent diseases such as glioblastoma.

Numerous attempts have been made to modulate PK activity. Examples are: biomimetic approaches using large molecules patterned on those involved in the actual cellular processes (e.g., mutant ligands (U.S. Pat. No. 4,966,849)); soluble receptors and antibodies (WO 94/10202, Kendall et al., *Proc. Nat'l Acad. Sci.* 90: 10705-09 (1994), Kim et al., *Nature* 362: 841-844 (1993)); RNA ligands (Jelinek et al., *Biochemistry* 33: 10450-56); Takano et al., *Mol. Bio. Cell* 4: 358A (1993); Kinsella et al., *Exo. Cell Res.* 199: 56-62 (1992); Wright et al., *J. Cellular Phys.* 152: 448-57); and tyrosine kinase inhibitors (WO 94/03427; WO 92/21660; WO 91/15495; WO 94/14808; U.S. Pat. No. 5,330,992; Mariani et al., *Proc. Am. Assoc. Cancer Res.* 35: 2268 (1994)). Despite such attempts, a need still exists for effective methods of modulating PK activity.

3. SUMMARY OF THE INVENTION

This invention encompasses compounds of formula I:

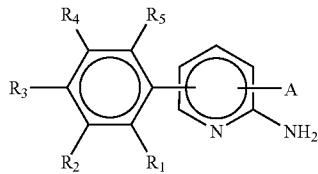

and pharmaceutically acceptable salts and solvates thereof, wherein:

A is

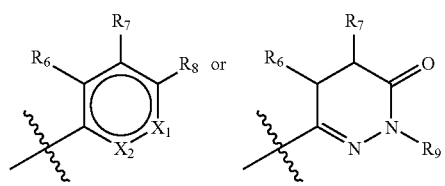

$X_1$ is —$CR_a$— or —N—, wherein $R_a$ is hydrogen, halogen or optionally substituted alkyl;

$X_2$ is —$CR_b$— or —N—, wherein $R_b$ is hydrogen, halogen or optionally substituted alkyl;

each of $R_1$, $R_2$, $R_3$, $R_4$, $R_5$ is independently hydrogen, halogen, or optionally substituted heterocycle;

each of $R_6$ and $R_7$ is independently hydrogen, halogen or optionally substituted alkyl;

$R_8$ is an optionally substituted heterocycle or —$NR_cR_d$, —$C(O)NR_cR_d$, or —$C(O)R_e$, wherein each of $R_c$, $R_d$ and $R_e$ is independently hydrogen or optionally substituted alkyl; and $R_9$ is hydrogen or optionally substituted alkyl.

A specific embodiment encompasses compounds of Formula II:

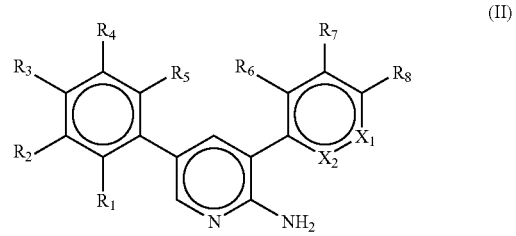

Another specific embodiment of the invention encompasses compounds of Formula III:

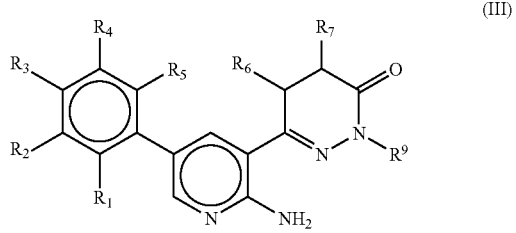

Another embodiment of the invention encompasses methods of treating, managing and preventing diseases and disorders, which comprise administering to a patient in need thereof a therapeutically or prophylactically effective amount of a compound of the invention (e.g., a compound of Formula I, II or III).

4. DETAILED DESCRIPTION

This invention relates to aryl pyridines and related compounds, and methods of their use for the treatment, prevention and management of various diseases and disorders.

4.1. Definitions

Unless otherwise indicated, the term "alkyl" means a saturated straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Examples of cycloalkyl groups include, but are not limited to, cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes "alkenyl" and "alkynyl" moieties.

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "aryl" means a an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" means a heteroaryl moiety bound to an alkyl moeity.

Unless otherwise indicated, the term "heterocycle" refers to an aromatic, partially aromatic or non-aromatic, monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocycloalkyl" means a non-aromatic heterocycle.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol (e.g., hydroxyl, alkyl-OH), aldehylde, alkanoyloxy, alkoxycarbonyl, alkyl (e.g., methyl, ethyl, propyl, t-butyl), alkenyl, alkynyl, amide, amine (primary, secondary and tertiary such as alkylamino, arylamino, arylalkylamino), aroyl, aryl, aryloxy, azo, carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, imine (primary and secondary), isocyanate, isothiocyanate, ketone, halo, haloalkyl (e.g., fluoromethyl, difluoromethyl, trifluoromethyl), hemiacetal, heterocycle, nitrile, nitro, phosphodiester, sulfide, sulfonamido (e.g., SO$_2$NH$_2$), sulfone, sulfonyl (including alkylsulfonyl, arylsulfonyl and arylalkylsulfonyl), sulfoxide and thiol (e.g., sulfhydryl, thioether).

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise specified, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol (e.g., hydroxyl, alkyl-OH), aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)R), amide (—C(O)NHR— or —RNHC(O)—), amidinyl (—C(NH)NHR or —C(NR)NH$_2$), amine (primary, secondary and tertiary such as alkylamino, arylamino, arylalkylamino), aroyl, aryl, aryloxy, azo, carbamoyl (—NHC(O)OR— or —OC(O)NHR—), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NH-CONHR—).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to." Similarly, the term "includes" has the same meaning as "includes, but is not limited to."

Unless otherwise indicated, an adjective before a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that if there is a discrepancy between a depicted structure and a name given that structure, the structure should be accorded more weight. In addition, if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences.

4.2. Compounds and Methods of Synthesis

This invention encompasses compounds of formula I:

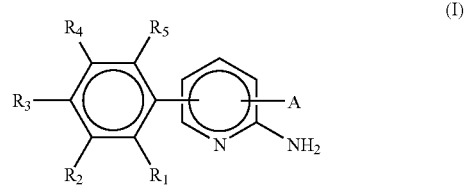

and pharmaceutically acceptable salts and solvates thereof, wherein:

A is

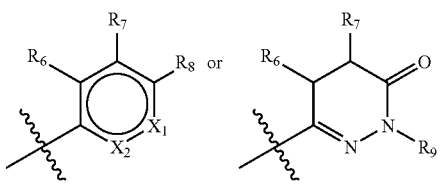

$X_1$ is —CR$_a$— or —N—, wherein R$_a$ is hydrogen, halogen or optionally substituted alkyl;

$X_2$ is —CR$_b$— or —N—, wherein R$_b$ is hydrogen, halogen or optionally substituted alkyl;

each of $R_1$, $R_2$, $R_3$, $R_4$, $R_5$ is independently hydrogen, halogen, or optionally substituted heterocycle;

each of $R_6$ and $R_7$ is independently hydrogen, halogen or optionally substituted alkyl;

$R_8$ is an optionally substituted heterocycle or —NR$_c$R$_d$, —C(O)NR$_c$R$_d$, or —C(O)R$_e$, wherein each of R$_c$, R$_d$ and R$_e$ is independently hydrogen or optionally substituted alkyl; and $R_9$ is hydrogen or optionally substituted alkyl.

In one embodiment, $R_1$ and $R_2$, $R_2$ and $R_3$, $R_3$ and $R_4$, or $R_4$ and $R_5$, together with the carbon atoms to which they are attached, form a pyrrolidinone ring.

In one embodiment, if $X_1$ is —CH—, $X_2$ is —CH—, and each of $R_1$-$R_7$ is hydrogen, then $R_8$ is not NH$_2$.

One embodiment of the invention encompasses compounds of Formula II:

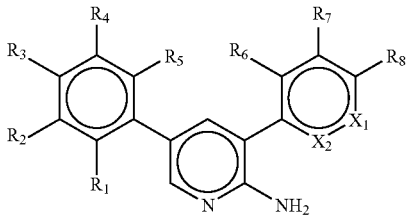

In a specific embodiment, if $X_1$ is —CH—, $X_2$ is —CH—, and each of $R_1$-$R_7$ is hydrogen, then $R_8$ is not $NH_2$.

Another embodiment encompasses compounds of Formula III:

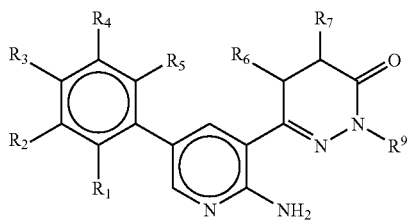

In another embodiment, $R_1$ is the same as $R_5$. In another embodiment, $R_1$ is the same as $R_4$ and $R_5$. In another embodiment, $R_1$ is hydrogen.

In another embodiment, $R_2$ is an optionally substituted heterocycle. In a specific embodiment, the heterocycle is a heteroaryl. In another, the heterocycle is thiazole, tetrazole or piperidine.

In another embodiment, $R_3$ is hydrogen.
In another embodiment, $R_4$ is hydrogen.
In another embodiment, $R_5$ is hydrogen.
In another embodiment, $R_6$ is the same as $R_7$. In another embodiment, $R_6$ is hydrogen.
In another embodiment, $R_7$ is hydrogen.
In another embodiment, $R_6$ and $R_7$ are both hydrogen, $X_1$ is —$CR_a$— and $X_2$ is —N—. In another embodiment, $R_6$ and $R_7$ are both hydrogen, $X_1$ is —N— and $X_2$ is —$CR_b$—.

In another embodiment, both $X_1$ and $X_2$ are —N—. In another embodiment, $X_1$ is —$CR_a$— and $X_2$ is —$CR_b$—. In a specific embodiment, $R_b$ is halogen.

In another embodiment, $R_8$ is —C(O)$NH_2$. In another embodiment, $R_8$ is —C(O)-alkyl. In another embodiment, $R_8$ is tetrazole.

Examples of specific compounds encompassed by the invention include:
4-(2-amino-5-(3-(2-aminothiazol-4-yl)phenyl)pyridin-3-yl)benzamide;
4-(2-amino-5-(3-(piperidin-4-yl)phenyl)pyridin-3-yl)benzamide;
4-(5-(3-(1H-tetrazol-5-yl)phenyl)-2-aminopyridin-3-yl)-2-fluorobenzamide;
4-(2-amino-5-(2-oxoindolin-5-yl)pyridin-3-yl)benzamide;
4-(5-(3-(1-acetylpiperidin-4-yl)phenyl)-2-aminopyridin-3-yl)benzamide;
4-(2-amino-5-(3-(1-methyl-1H-tetrazol-5-yl)phenyl)pyridin-3-yl)-2-fluorobenzamide;
4-(5-(3-(1-acetylpiperidin-4-yl)phenyl)-2-aminopyridin-3-yl)-2,6-difluorobenzamide;
4-(2-amino-5-(3-(2-methyl-2H-tetrazol-5-yl)phenyl)pyridin-3-yl)-2-fluorobenzamide;
1-(4-(2-amino-5-(4-fluorophenyl)pyridin-3-yl)phenyl)pentan-1-one;
6-(2-amino-5-(4-fluorophenyl)pyridin-3-yl)pyridazin-3-amine;
6-(2-amino-5-(4-fluorophenyl)pyridin-3-yl)pyridazin-3(2H)-one; and
3-(4-(2H-tetrazol-5-yl)phenyl)-5-(4-fluorophenyl)pyridin-2-amine.

Compounds of the invention may contain one or more stereocenters, and may exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, NY, 1962); and Wilen, S. H., *Tables of Resolving Agents and Optical Resolutions*, p. 268 (E. L. Eliel, Ed., Univ. of Notre Dame Press, Notre Dame, Ind., 1972).

This invention further encompasses stereoisomeric mixtures of compounds disclosed herein. It also encompasses configurational isomers of compounds disclosed herein, either in admixture or in pure or substantially pure form, such as cis (Z) and trans (E) alkene isomers.

Compounds of the invention can be prepared using methods known in the art. They can also be prepared using the general approach shown below:

Scheme I

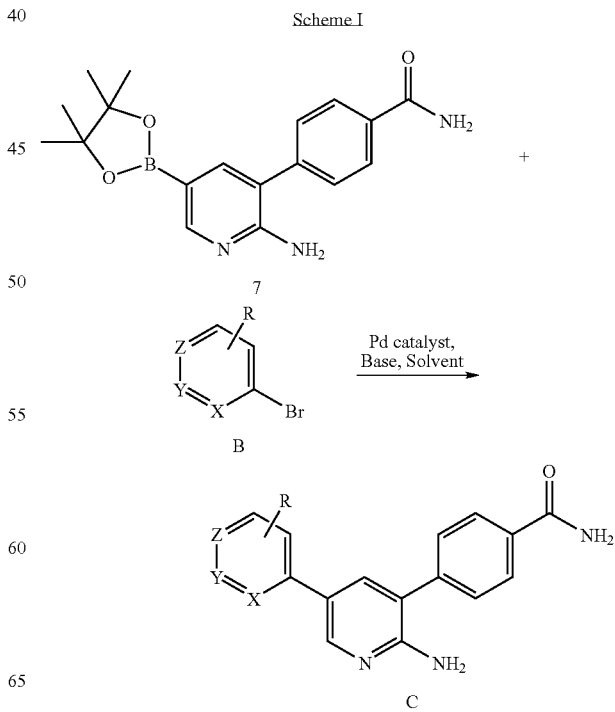

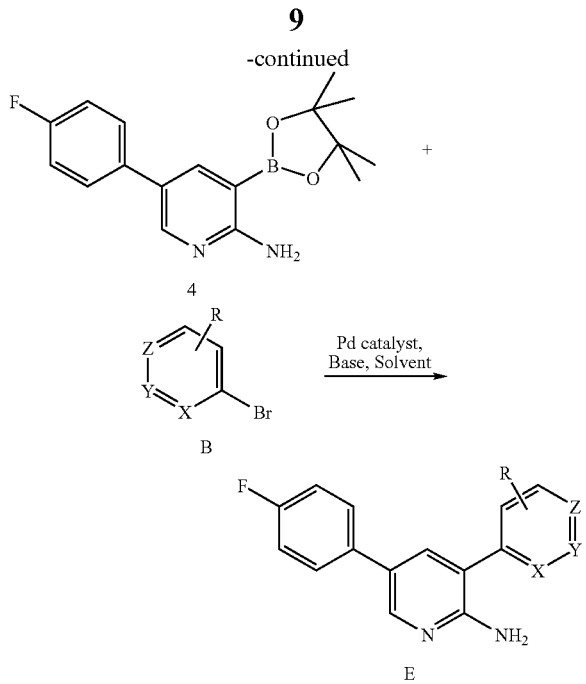

In this approach, Z, Y, and X are typically CH groups. Compounds C and E are synthesized via Suzuki coupling of boron pinicolate esters, such as compounds 7 and 4, respectively. The pinicolate esters are coupled with a heterocyclic bromide to give the desired target compounds, C and E. Syntheses of specific compounds are discussed in the examples, below.

4.3. Methods of Use

This invention encompasses methods of treating, managing and preventing diseases and disorders, which comprise administering to a patient (a mammal, e.g., human) in need thereof a therapeutically or prophylactically effective amount of a compound disclosed herein. Examples of diseases and disorders include primary and secondary immunodeficiency disorders, hypersensitivity disorders, pulmonary disorders, gastrointestinal disorders, and cancer.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation.

4.4. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin, Captisol®, and Encapsin™ (see generally Davis and Brewster, 2004, *Nat. Rev. Drug Disc.* 3:1023-1034), Labrasol®, Labrafil®, Labrafac®, cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:cornoil).

Poorly soluble compounds may also be incorporated into suspensions using other techniques known in the art. For example, nanoparticles of a compound may be suspended in a liquid to provide a nanosuspension (see generally Rabinow, 2004, *Nature Rev. Drug Disc.* 3:785-796). Nanoparticle forms of compounds described herein may be prepared by the methods described in U.S. Patent Publication Nos. 2004-0164194, 2004-0195413, 2004-0251332, 2005-0042177 A1, 2005-0031691 A1, and U.S. Pat. Nos. 5,145,684, 5,510,118, 5,518,187, 5,534,270, 5,543,133, 5,662,883, 5,665,331, 5,718,388, 5,718,919, 5,834,025, 5,862,999, 6,431,478, 6,742,734, 6,745,962, the entireties of each of which are incorporated herein by reference. In one embodiment, the nanoparticle form comprises particles having an average particle size of less than about 2000 nm, less than about 1000 nm, or less than about 500 nm.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

4.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

4.4.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.4.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.4. Delayed and Extended Release Dosage Forms

Compounds of the invention may be administered by controlled release (e.g., delayed release and extended release) means known in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.5. Kits

This invention encompasses kits which can simplify the administration of one or more active ingredients to a patient. A typical kit comprises single unit dosage form(s) of one or more active ingredients (e.g., a compound of the invention), in addition to one or more devices that may be used to administer the active ingredient(s). Examples of such devices include, but are not limited to, syringes, drip bags, patches, and inhalers.

Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4.4.6. Compositions with Enhanced Stability

The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are specifically anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are specifically packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

5. EXAMPLES

Aspects of this invention may be understood from the following examples, which do not limit its scope.

5.1. Synthesis of 2-amino-3-(boronpinacolate)-5-(4-fluorophenyl)pyridine

To a mixture of 2-amino-5-bromopyridine 1 (1.80 g, 10.4 mmol) in 104 ml toluene and 24 ml ethanol (EtOH) was added 4-fluorophenyl boronic acid (1.75 g, 12.5 mmol) followed by 10 ml of 2.0 M aqueous $Na_2CO_3$. The reaction was degassed with nitrogen and $Pd(PPh_3)_4$ (0.60 g, 0.52 mmol) was added in one portion and the reaction was heated to reflux for 26 hours. The reaction was then cooled to ambient temperature and diluted with 50 ml water. The layers were separated and the aqueous layer was extracted with ethyl acetate (EtOAc) (2×100 mL). The organic layers were combined, washed with saturated aqueous $NaHCO_3$, dried over $MgSO_4$ and concentrated to a brown oil. Automated purification on a silica gel ISCO column (120 g column, 2.5% MeOH—$CH_2Cl_2$) gave 1.20 g (60%) of 2-amino-5-(4-fluorophenyl)pyridine as a yellow solid.

To a solution of 2-amino-5-(4-fluorophenyl)pyridine (0.80 g, 4.25 mmol) in 20 ml glacial acetic acid was added sodium acetate (1.39 g, 17.0 mmol). Subsequently, a solution of bromine (0.44 mL, 8.50 mmol) in 2 ml glacial acetic acid was added dropwise to the reaction by addition funnel. After the addition, the reaction was heated to reflux for 1 hour then cooled and diluted with dichloromethane. The solution was washed with 25 ml saturated aqueous sodium hydrogen sulfate and then 25 ml water then dried over magnesium sulfate and concentrated to a brown oil. Automated purification on a silica gel ISCO column (120 g column, 2.5% MeOH—$CH_2Cl_2$) gave 1.20 g (60%) of 2-amino-3-bromo-5-(4-fluorophenyl)pyridine as an off-white/pink solid.

Anhydrous 1,4-dioxane (10 mL) was purged with dry nitrogen and $Pd_2(dba)_3$ (243 mg, 0.42 mmol) and $PCy_3$ (284 mg, 1.01 mmol) was added and the mixture stirred for 30 minutes. Next, bis(pinacolato)diboron (2.68 g, 10.6 mmol), KOAc (1.04 g, 10.6 mmol) and 2-amino-3-bromo-5-(4-fluorophenyl)pyridine (1.80 g, 7.04 mmol) were added and the reaction was heated to 80° C. for 3 hours. The reaction was then cooled, diluted with 25 ml $H_2O$ and extracted with EtOAc 100 mL. The layers were separated and the aqueous layer was again extracted with EtOAc (2×50 mL). The organic layers were combined, washed with saturated aqueous brine, dried over NaSO and concentrated to give 2-amino- 3-(boronpinacolate)-5-(4-fluorophenyl)pyridine as a pale yellow solid and used without further purification.

5.2. Synthesis of 2-amino-5-(boronpinacolate)-3-(4-phenylcarboxamide)

To a sealed tube apparatus containing 2-amino-3-bromo-5-chloropyridine (1.0 g, 4.9 mmol) dissolved in 20 ml dimethylformamide (DMF) was added 4-carbamidylphenyl boronic acid (1.6 g, 10.3 mmol) followed by potassium carbonate (1.3 g, 9.4 mmol). Next, PddppfCl$_2$ (0.2 g, 0.02 mmol) was added and the tube was sealed and heated to 170° C. and stirred overnight. The reaction was cooled to ambient temperature and the solvent was evaporated. The residue was redissolved in 60 ml of 1N aqueous HCl and washed with 30 ml of ethyl acetate. The pH of the aqueous layer was then adjusted to 7-8 by adding 1N aqueous NaOH and a white solid precipitated and was collected by filtration to give 1.05 g of 4-(2-amino-5-chloropyridin-3-yl)benzamide (88%).

4-(2-Amino-5-chloropyridin-3-yl)benzamide (0.5 g, 2.0 mmol) was dissolved in 20 ml DMF in a predried seal tube apparatus and bis(pinacolato)diboron (1.02 g, 4.02 mmol, potassium acetate (0.395 g, 4.02 mmol) and tricyclohexyl phosphine (0.14 g, 0.48 mmol) were added. After purging the mixture with nitrogen gas for 10 minutes, Pd(dba)$_2$ (0.115 g, 0.2 mmol) was added and the reaction vessel was sealed and heated 175° C. overnight. The reaction was then cooled and evaporated under reduced pressure. The residue was taken up in 40 ml ethyl acetate and transferred to a separatory funnel and extracted with 1N aqueous HCl (2×50 mL). The aqueous phases were combined and adjusted the pH to 4-5 and the water was removed under reduced pressure. The residue was taken up in 50 ml of isopropanol and the NaCl was removed by filtration. The isopropanol was evaporated under reduced pressure to give 2-amino-5-(boronpinacolate)-3-(4-phenylcarboxamide) as an off-white solid that was used without further purification.

5.3. Synthesis of 4-[2-Amino-5-(3-piperidin-4-yl-phenyl)-pyridin-3-yl]-benzamide 2-Amino-5-(boronpinacolate)-3-(4-phenylcarboxamide) (50 mg, 0.2 mmol) was dissolved in 5 ml of toluene and 1 ml of ethanol and 4-(3-Bromo-phenyl)-piperidine (96 mg, 0.4 mmol) was added followed by 2 ml of 2.0 M aqueous sodium carbonate. Next, Pd(PPh$_3$)$_4$ (15 mg, 0.01 mmol) was added and the reaction was heated to reflux for 3 hours. The solvent was removed under reduced pressure and the residue was taken up in 30 ml of ethyl acetate and 20 ml of water. After shaking in a separatory funnel, the organic phase was dried over Na$_2$SO$_4$ and evaporated and the residue was purified by preparatory-HPLC and lyophilized to give 4-(2-amino-5-(3-(piperidin-4-yl)phenyl)pyridin-3-yl)benzamide as a white solid.

5.4. Synthesis of 4-{2-Amino-5-[3-(2-amino-thiazol-4-yl)-phenyl]-pyridin-3-yl}-benzamide 2-Amino-5-(boronpinacolate)-3-(4-phenylcarboxamide) was coupled to commercially available 4-(3-bromo-phenyl)-thiazol-2-ylamine using the method described in Example 3 to give 4-{2-amino-5-[3-(2-amino-thiazol-4-yl)-phenyl]-pyridin-3-yl}-benzamide as the target compound. MH$^+$=388.

5.5. Synthesis of 4-[2-Amino-5-(3-piperidin-4-yl-phenyl)-pyridin-3-yl]-benzamide 2-Amino-5-(boronpinacolate)-3-(4-phenylcarboxamide) was coupled to commercially available 4-(3-bromo-phenyl)-piperidine using the method described in Example 3 to give 4-[2-amino-5-(3-piperidin-4-yl-phenyl)-pyridin-3-yl]-benzamide as the target compd. MH$^+$=373.

5.6. Synthesis of 4-[2-Amino-5-(2-oxo-2,3-dihydro-1H-indol-5-yl)-pyridin-3-yl]-benzamide 2-Amino-5-(boronpinacolate)-3-(4-phenylcarboxamide) was coupled to commercially available 5-bromo-1,3-dihydro-indol-2-one using the method described in Example 3 to give 4-[2-amino-5-(2-oxo-2,3-dihydro-1H-indol-5-yl)-pyridin-3-yl]-benzamide as the target compound. MH$^+$=345.

5.7. Synthesis of 4-{2-Amino-5-[3-(1H-tetrazol-5-yl)-phenyl]-pyridin-3-yl}-2-fluoro-benzamide 2-Amino-3-bromo-5-chloropyridine was coupled to 3-fluoro-4-carbamidylphenyl boronic acid using the method described in Example 2. Then, using the method described in Example 2 followed by the method described in Example 3, the boronate ester was installed and then coupled to commercially available 5-(3-bromo-phenyl)-1-methyl-1H-tetrazole to give 4-{2-amino-5-[3-(1H-tetrazol-5-yl)-phenyl]-pyridin-3-yl}-2-fluoro-benzamide as the target compound. MH$^+$=390.

5.8. Synthesis of 4-{5-[3-(1-Acetyl-piperidin-4-yl)-phenyl]-2-amino-pyridin-3-yl}-benzamide 2-Amino-5-(boronpinacolate)-3-(4-phenylcarboxamide) was coupled to commercially available 1-[4-(3-bromo-phenyl)-piperidin-1-yl]-ethanone using the method described in Example 3 to give 4-{5-[3-(1-acetyl-piperidin-4-yl)-phenyl]-2-amino-pyridin-3-yl}-benzamide as the target compound. MH$^+$=415.

5.9. Synthesis of 4-{2-Amino-5-[3-(1-methyl-1H-tetrazol-5-yl)-phenyl]-pyridin-3-yl}-2-fluoro-benzamide 2-Amino-3-bromo-5-chloropyridine was coupled to 3-fluoro-4-carbamidylphenyl boronic acid using the method described in Example 2. Then, using the method described in Example 2 followed by the method described in Example 3, the boronate ester was installed and then coupled to commercially available 5-(3-bromo-phenyl)-1-methyl-1H-tetrazole to give 4-{2-amino-5-[3-(1-methyl-1H-tetrazol-5-yl)-phenyl]-pyridin-3-yl}-2-fluoro-benzamide. MH$^+$=390.

5.10. Synthesis of 4-{5-[3-(1-Acetyl-piperidin-4-yl)-phenyl]-2-amino-pyridin-3-yl}-2,6-difluoro-benzamide 2-Amino-3-bromo-5-chloropyridine was coupled to 3,5-difluoro-4-carbamidylphenyl boronic acid using the method described in Example 2. Then, using the method described in Example 2 followed by the method described in Example 3, the boronate ester was installed and then coupled to commercially available 1-[4-(3-bromo-phenyl)-piperidin-1-yl]-ethanone to give 4-{5-[3-(1-acetyl-piperidin-4-yl)-phenyl]-2-amino-pyridin-3-yl}-2,6-difluoro-benzamide. MH$^+$=451.

5.11. Synthesis of 4-{2-Amino-5-[3-(2-methyl-2H-tetrazol-5-yl)-phenyl]-pyridin-3-yl}-2-fluoro-benzamide 2-Amino-3-bromo-5-chloropyridine was coupled to 3-fluoro-4-carbamidylphenyl boronic acid using the method described in Example 2. Then, using the method described in Example 2 followed by the method described in Example 3, the boronate ester was installed and then coupled to commercially available 5-(3-bromo-phenyl)-2-methyl-2H-tetrazole to give 4-{2-amino-5-[3-(3-methyl-2H-tetrazol-5-yl)-phenyl]-pyridin-3-yl}-2-fluoro-benzamide. MH⁺=390.

5.12. Synthesis of 1-{4-[2-Amino-5-(4-fluorophenyl)-pyridin-3-yl]-phenyl}-pentan-1-one

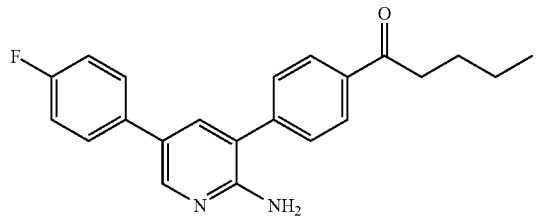

2-Amino-3-(boronpinacolate)-5-(4-fluorophenyl)pyridine was coupled to commercially available 1-(4-bromo-phenyl)-pentan-1-one using the method described in Example 3 to give 1-{4-[2-amino-5-(4-fluoro-phenyl)-pyridin-3-yl]-phenyl}-pentan-1-one as the target compound. MH⁺=349.

5.13. Synthesis of 6-[2-Amino-5-(4-fluoro-phenyl)-pyridin-3-yl]-pyridazin-3-ylamine

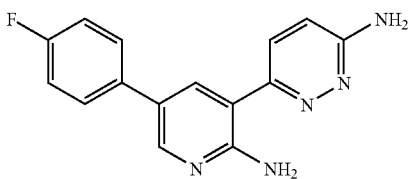

2-Amino-3-(boronpinacolate)-5-(4-fluorophenyl)pyridine was coupled to commercially available 6-bromo-pyridazin-3-ylamine using the method described in Example 3 to give 6-[2-amino-5-(4-fluoro-phenyl)-pyridin-3-yl]-pyridazin-3-ylamine as the target compound. MH⁺=281.

5.14. Synthesis of 6-[2-Amino-5-(4-fluoro-phenyl)-pyridin-3-yl]-4,5-dihydro-2H-pyridazin-3-one 2-Amino-3-(boronpinacolate)-5-(4-fluorophenyl)pyridine was coupled to commercially available 6-bromo-4,5-dihydro-2H-pyridazin-3-one using the method described in Example 3 to give 6-[2-amino-5-(4-fluoro-phenyl)-pyridin-3-yl]-4,5-dihydro-2H-pyridazin-3-one as the target compound. MH⁺=285.

5.15. Synthesis of 5-(4-Fluoro-phenyl)-3-[4-(2H-tetrazol-5-yl)-phenyl]-pyridin-2-ylamine 2-Amino-3-(boronpinacolate)-5-(4-fluorophenyl)pyridine was coupled to commercially available 5-(4-bromo-phenyl)-2H-tetrazole using the method described in Example 3 to give 5-(4-Fluoro-phenyl)-3-[4-(2H-tetrazol-5-yl)-phenyl]-pyridin-2-ylamine as the target compound. MH⁺=333.

All cited publications, patents, and patent applications are herein incorporated by reference in their entireties.

What is claimed is:

1. A compound of formula I:

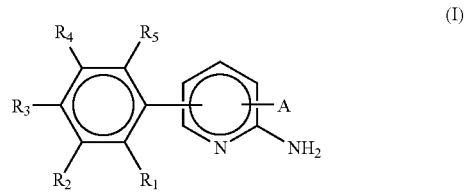

or a pharmaceutically acceptable salt or solvate thereof, wherein:

A is

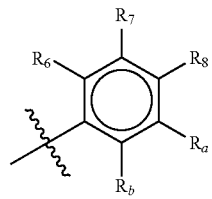

$R_a$ is hydrogen, halogen or optionally substituted alkyl;

$R_b$ is hydrogen, halogen or optionally substituted alkyl;

each of $R_1$, $R_2$, $R_3$, $R_4$, $R_5$ is independently hydrogen, halogen, or optionally substituted heterocycle; or $R_1$ and $R_2$, $R_2$ and $R_3$, $R_3$ and $R_4$, or $R_4$ and $R_5$, together with the carbon atoms to which they are attached, form a pyrrolidinone ring;

each of $R_6$ and $R_7$ is independently hydrogen, halogen or optionally substituted alkyl; and $R_8$ is an optionally substituted heterocycle or —$NR_cR_d$, —$C(O)NR_cR_d$, or —$C(O)R_e$, wherein each of $R_c$, $R_d$ and $R_e$ is independently hydrogen or optionally substituted alkyl;

provided that if each of $R_a$, $R_b$ and $R_1$-$R_7$ is hydrogen, then $R_8$ is not $NH_2$.

2. The compound of claim 1, wherein $R_1$ is the same as $R_5$.

3. The compound of claim 1, wherein $R_1$ is the same as $R_4$ and $R_5$.

4. The compound of claim 1, wherein $R_1$ is hydrogen.

5. The compound of claim 1, wherein $R_2$ is an optionally substituted Heterocycle.

6. The compound of claim 1, wherein $R_3$ is hydrogen.

7. The compound of claim 1, wherein $R_4$ is hydrogen.

8. The compound of claim 1, wherein $R_5$ is hydrogen.

9. The compound of claim 1, wherein $R_6$ is the same as $R_7$.

10. The compound of claim 1, wherein $R_6$ is hydrogen.

11. The compound of claim 1, wherein $R_7$ is hydrogen.

12. The compound of claim 1, wherein $R_8$ is —$C(O)NH_2$.

13. The compound of claim 1, wherein $R_8$ is —$C(O)$-alkyl.

14. The compound of claim 1, wherein $R_8$ is tetrazole.

15. A compound of formula II:

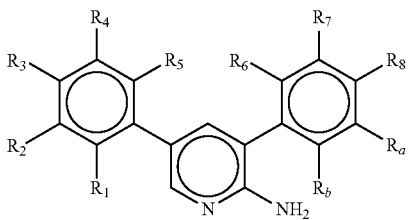

or a pharmaceutically acceptable salt or solvate thereof, wherein:

$R_a$ is hydrogen, halogen or optionally substituted alkyl;
$R_b$ is hydrogen, halogen or optionally substituted alkyl;
each of $R_1$, $R_2$, $R_3$, $R_4$, $R_5$ is independently hydrogen, halogen, or optionally substituted heterocycle; or $R_1$ and $R_2$, $R_2$ and $R_3$, $R_3$ and $R_4$, or $R_4$ and $R_5$, together with the carbon atoms to which they are attached, form a pyrrolidinone ring;
each of $R_6$ and $R_7$ is independently hydrogen, halogen or optionally substituted alkyl; and
$R_8$ is an optionally substituted heterocycle or —$NR_cR_d$, —$C(O)NR_cR_d$, or —$C(O)R_e$,
wherein each of $R_c$, $R_d$ and $R_e$ is independently hydrogen or optionally substituted alkyl;
provided that if each of $R_a$, $R_b$ and $R_1$-$R_7$ is hydrogen, then $R_8$ is not $NH_2$.

* * * * *